United States Patent [19]

Coleman et al.

[11] Patent Number: 5,686,597
[45] Date of Patent: Nov. 11, 1997

[54] THROMBIN RECEPTOR HOMOLOG

[75] Inventors: Roger Coleman, Mountain View; Janice Au-Young, Berkeley; Olga Bandman, Mountain View; Jeffrey J. Seilhamer, Los Altos Hills, all of Calif.

[73] Assignee: Incyte Pharmaceuticals, Inc., Palo Alto, Calif.

[21] Appl. No.: 467,125

[22] Filed: Jun. 6, 1995

[51] Int. Cl.$^6$ .................................. C12N 15/12
[52] U.S. Cl. ...................... 536/23.5; 435/2; 435/7.21; 435/65.1; 435/240.1; 435/240.2; 435/252.3; 435/254.11
[58] Field of Search ................ 435/254.11, 69.1, 435/2, 252.3, 240.1, 7.21, 240.2; 536/23.5

[56] References Cited

U.S. PATENT DOCUMENTS 5,256,766  10/1993  Coughlin et al. .................. 530/327
5,516,889   5/1996  Hollenberg ........................ 530/317

FOREIGN PATENT DOCUMENTS

WO 92/14750  9/1996  WIPO.

OTHER PUBLICATIONS

Vu et al. (1991) Cell 64: 1057–1068.
Rasmussen et al. (1991) FEBS 288: 123–128.
Wilcox et al., "Characterization of Thrombin Receptor Expression During Vascular Lesion Formulation." *Cir. Res.* 75(6):1029–1038 (Dec. 1994).

Brass et al., "Structure and Function of the Human Platelet Thrombin Receptor" *J. Biol. Chem.* 267(20):13795–13798 (Jul. 15, 1992).

Dennington et al., "The thrombin receptor," *Clin. Exp. Pharmacol. Physiol.* 21:349–358 (1994).

*Primary Examiner*—Stephen Walsh
*Assistant Examiner*—Kenneth A. Sorensen
*Attorney, Agent, or Firm*—Incyte Pharmaceuticals; Lucy J. Billings; Barbara J. Luther

[57] ABSTRACT

The present invention provides nucleotide and amino acid sequences that identify and encode a novel thrombin receptor homolog (TRH) expressed in human liver. The present invention also provides for antisense molecules to the nucleotide sequences which encode TRH, diagnostic tests based on TRH encoding nucleic acid molecules, expression vectors for the production of purified TRH, antibodies capable of binding specifically to TRH, hybridization probes or oligonucleotides for the detection of TRH-encoding nucleotide sequences, genetically engineered host cells for the expression of TRH, and antagonists, antibodies and inhibitors with specific binding activity for the polypeptide TRH.

6 Claims, 5 Drawing Sheets

```
                9                 18                27                36                45                54
5' ATG AGA AGT CAT ACC ATA ACA ATG ACG ACA ACT TCA GTC AGC AGC TGG CCT TAC
   M   R   S   H   T   I   T   M   T   T   T   S   V   S   S   W   P   Y 63                72                81                90                99               108
   TCC TCC CAC AGA ATG CGC TTT ATA ACC AAT CAT AGC GAC CAA CCG CCA CAA AAC
   S   S   H   R   M'  R   F   I   T   N   H   S   D   Q   P   P   Q   N 117               126               135               144               153               162
   TTC TCA GCA ACA CCA AAT GTT ACT ACC TGT CCC ATG GAT GAA AAA TTG CTA TCT
   F   S   A   T   P   N   V   T   T   C   P   M   D   E   K   L   L   S 171               180               189               198               207               216
   ACT GTG TTA ACC ACA TCC TAC TCT GTT ATT TTC ATC GTG GGA CTG GTT GGG AAC
   T   V   L   T   T   S   Y   S   V   I   F   I   V   G   L   V   G   N 225               234               243               252               261               270
   ATA ATC GCC CCC TAT GTA TTT CTG GGT ATT CAC CGT AAA AGA AAT TCC ATT CAA
   I   I   A   P   Y   V   F   L   G   I   H   R   K   R   N   S   I   Q 279               288               297               306               315               324
   ATT TAT CTA CTT AAC GTA GCC ATT GCA GAC CTC CTA CTC ATC TTC TGC CTC CCT
   I   Y   L   L   N   V   A   I   A   D   L   L   L   I   F   C   L   P 333               342               351               360               369               378
   TTC CGA ATA ATG TAT CAT ATT AAC CAA AAC AAG TGG ACA CTA GGT GTG ATT CTG
   F   R   I   M   Y   H   I   N   Q   N   K   W   T   L   G   V   I   L 387               396               405               414               423               432
   TGC AAG GTT GTG GGA ACA CTG CTT TAT ATG AAC ATG TAC ATT AGC ATT ATT TTG
   C   K   V   V   G   T   L   L   Y   M   N   M   Y   I   S   I   I   L 441               450               459               468               477               486
   CTT GGA TTC ATC AGT TTG GAT CGC TAT ATA AAA ATT AAT CGG TCT ATA CAG CAA
   L   G   F   I   S   L   D   R   Y   I   K   I   N   R   S   I   Q   Q 495               504               513               522               531               540
   CGG AAG GCA ATA ACA ACC AAA CAA AGT ATT TAT GTC TGT TGT ATA GTA TGG ATG
   R   K   A   I   T   T   K   Q   S   I   Y   V   C   C   I   V   W   M 549               558               567               576               585               594
   CTT GCT CTT GGT GGA TTC CTA ACT ATG ATT ATT TTA ACA CTT AAG AAA GGA GGG
   L   A   L   G   G   F   L   T   M   I   I   L   T   L   K   K   G   G 603               612               621               630               639               648
   CAT AAT TCC ACA ATG TGT TTC CAT TAC AGA GAT AAG CAT AAC GCA AAA GGA GAA
   H   N   S   T   M   C   F   H   Y   R   D   K   H   N   A   K   G   E 657               666               675               684               693               702
   GCC ATT TTT AAC TTC ATT CTT GTG GTA ATG TTC TGG CTA ATT TTC TTA CTA ATA
   A   I   F   N   F   I   L   V   V   M   F   W   L   I   F   L   L   I
```

FIGURE 1A

```
        711             720             729             738             747             756
ATC CTT TCA TAT ATT AAG ATT GGG AAG AAT CTA TTG AGG ATT TCT AAA AGG AGG
 I   L   S   Y   I   K   I   G   K   N   L   L   R   I   S   K   R   R 765             774             783             792             801             810
TCA AAA TTT CCT AAT TCT GGT AAA TAT GCC ACT ACA GCT CGT AAC TCC TTT ATT
 S   K   F   P   N   S   G   K   Y   A   T   T   A   R   N   S   F   I 819             828             837             846             855             864
GTA CTT ATC ATT TTT ACT ATA TGT GTG GGT CCC TAT CAT GCC TTT CGA TTC ATC
 V   L   I   I   F   T   I   C   V   G   P   Y   H   A   F   R   F   I 873             882             891             900             909             918
TAC ATT TCT TCA CAG CTA AAT GTA TCA TCT TGC TAC TGG AAA GAA ATT GTT CAC
 Y   I   S   S   Q   L   N   V   S   S   C   Y   W   K   E   I   V   H 927             936             945             954             963             972
AAA ACC AAT GAG ATC ATG CTG GTT CTC TCA TCT TTC AAT AGT TGG TTA GAT CCA
 K   T   N   E   I   M   L   V   L   S   S   F   N   S   W   L   D   P 981             990             999            1008            1017            1026
GTC ATG TAT TTC CTG ATG TCC AGT AAC ATT CGC AAA ATA ATG TGC CAA CTT CTT
 V   M   Y   F   L   M   S   S   N   I   R   K   I   M   C   Q   L   L 1035            1044            1053            1062            1071            1080
TTT AGA CGA TTT CAA GGT GAA CCA AGT AGG AGT GAA AGC ACT TCA GAA TTT AAA
 F   R   R   F   Q   G   E   P   S   R   S   E   S   T   S   E   F   K 1089            1098            1107            1116            1125            1134
CCA GGA TAC TCC CTG CAT GAT ACA TCT GTG GCA GGG AAA ATA CAG TCT AGT TCT
 P   G   Y   S   L   H   D   T   S   V   A   G   K   I   Q   S   S   S

1143
GAA AGT ACT 3'
 E   S   T
```

```
     . . . Q . . . . . . . . . . T . . . . . . . C . . W . L A . . G . . . . . . .    Consensus #1
     F L A V V R S I Q S L S A I T L G Q A I F V C L A V W A L A L G G V V T L V L K  Majority
     201                     210                 220                 230             240
     F L A V V Y P M Q S L S W R T L G R A S F T C L A I W A L A I A G V V P L V L K  thrombin R
     153 Y I K I N R S I Q Q R K A I T T K Q S I Y V C C I V W M L A L G G F L T M I I -  86700

. . . T . . . G . N . T . C . . . . . . . . . . . . . G . . . . . . . F . . . . . . V . F . .  Consensus #1
     E L T L Q V G G L N I T T C H D V L D E T L A E G E A A F N F S A I L A V F F F  Majority
     241                     250                 260                 270             280
     E Q T I Q V P G L N I T T C H D V L N E T L L E G Y Y A Y Y F S A F S A V F F F  thrombin R
     192 - L T L K K G G H N S T M C F H Y R D K H N A K G E A I F N F - - I L V V M F W  86700

. . . . . . . . . . Y . . I . . . L . . . . . . R . . K . . . . . . . . . . . A .    Consensus #1
     V I L L L I V S Y V V S I G K N L L S S A V A N R S S K F P S S G L F A S A A R  Majority
     281                     290                 300                 310             320
     V P L I I S T V C Y V S H I I R C L S S A V A N R S K K - - S R A L F L S A A -  thrombin R
     229 L I F L L I L S V I K H G K N L L R - - I S K R R S K F P N S G K Y A T T A R  86700

. . . . V . . I F . I C . G P . . . . . . . . . . . . . . . . . . . . . S . . . . . . . . Y . . .    Consensus #1
     N S F I V L I I F I I C V G P T N A L L I A H F I F L S S T L T V S A A Y F A E  Majority
     318                     330                 340                 350             360
     - - - V F C I F I I C F G P T N V L L I A H Y S F L S H T S T T E A A Y F A Y    thrombin R
     267 N S F I V L I I F T L C V G P Y H A F - - R F I Y I S Q L N V S S C Y W K E  86700

. . . . . . . . . . . . . . . S S . . . S . . D P . . Y . . . . S S . . . . . . . . L . . . . .    Consensus #1
     L V H K T N E I M V V V S S I S S W L D P V I Y F L A S S E I Q K I V Y S L L F  Majority
     354                     370                 380                 390             400
     L L C - - - - V C V S S I S S C I D P L I Y Y A S S E C Q R Y V V Y S I L C    Consensus #1
     304 I V H K T N E I M L V L S S F N S W L D P V M Y F L M S S N I R K I M C Q L L F  86700
```

```
                                                          S              T
              P S   S       S               S        T
    . . R K E S G D P S S . . S E S S G E L K A G K S L T D S S V A G N I I S S L L T    Consensus #1 Majority
                         ↑410              ↑420              ↑430
388 C K E S S D P S  S Y N S S G Q L M A S K M D T C S S N L N N S I Y K K L L T
344 R R F Q G E P S  R S E S T S E F K P G Y S L H D T S V A G K I Q S S S S E S T        thrombin R 86700
```

THROMBIN RECEPTOR HOMOLOG

FIELD OF THE INVENTION

This invention relates to nucleic acid and amino acid sequences of a new human thrombin receptor homolog and the use thereof for the diagnosis, prevention and treatment of disease.

BACKGROUND ART

The thrombin receptor is a G-protein coupled seven transmembrane receptor (T7G) which is present on platelets, endothelial cells, fibroblasts, mesangial cells, neural cells and smooth muscle cells. This receptor is activated by the irreversible cleavage of the extracellular, amino terminal sequence between $arg^{41}$ and $ser^{42}$ by thrombin or another serine protease. In normal endothelial cells, activation of the thrombin receptor stimulates intracellular Gq-protein mediated phosphoinositide metabolism and Gi-protein mediated adenylate cyclase inhibition. Additionally, endothelial cells secrete endothelin-derived relaxing factor (EDRF). Subsequently EDRF stimulates soluble guanylate cyclase release followed by formation of cyclic GMP and relaxation of smooth muscle. Another function of EDRF is the inhibition of platelet adhesion and aggregation which is beneficial to blood flow.

Wilcox et al (1994, Circ Res 75:1029–38) disclosed that in rat aorta smooth muscle, thrombin receptor expression increases soon after vascular injury and triggers cell proliferation in the neointima. Blocking the thrombin receptor's cleavage site with antibody halts thrombin-induced cell proliferation. Following cleavage and activation, thrombin receptors become desensitized, and they are internalized for recycling. Receptor recycling and replacement limit the duration of thrombin initiated events.

The thrombin receptor has at least four potential N-glycosylation sites, $Asn^{35}$, $Asn^{62}$, $Asn^{75}$, and $Asn^{259}$. The presence of carbohydrate greatly affects the differences in size and predicted mass reported for thrombin receptors. Moreover, glycosylation may account for as much as 30% of the mass of these receptors and apparently determines their distribution (Brass L. F. et al (1992) J Biol Chem 267:13795–8).

The thrombin receptor is classified with the nonneurokinin T7G receptors which include many glycoprotein hormone receptors such as those for luteinizing hormone (LH) and follicle stimulating hormone (FSH). They have very long N-termini, bind a common ligand structural motif with low affinity to activate the receptor, and rely on the N-termini and extracellular loops to impart high affinity and specificity (Bolander FF (1994) Molecular Endocrinology, Academic Press, San Diego, Calif.).

They are related to other T7Gs by their seven hydrophobic domains which span the plasma membrane and form a bundle of antiparallel α helices. These transmembrane segments (TMS) are designated by roman numerals I–VII and account for structural and functional features of the receptor. In most cases, the bundle forms a binding pocket; however, when the binding site must accommodate more bulky molecules, the extracellular N-terminal segment or one or more of the three extracellular loops participate in binding (Watson S and Arkinstall S (1994) The G-Protein Linked Receptor Facts Book, Academic Press, San Diego, Calif.) and in subsequent induction of conformational change in intracellular portions of the receptor. The activated receptor in turn, interacts with an intracellular G-protein complex which mediates further intracellular signalling activities including the production of second messengers such as cyclic AMP (cAMP), phospholipase C, inositol triphosphate or ion channel proteins.

The novel thrombin receptor homolog (trh) which is the subject of this patent application was identified among the cDNAs derived from a liver tissue library. Incyte Clone 86700 is most similar to HUMTHRR, the human thrombin receptor (cf Dennington PM and MC Berndt (1994) Clin Exp Pharmacol Physiol 21:349–58). Additionally, Incyte 86700 displays amino acid sequence similarity to platelet activating factor receptor (residues 94–155). These amino acids cover most of TMS III, the second intracellular loop, and TMS IV. Incyte 86700 was expressed in cells in the liver which is briefly described below.

The basic functional unit of the human liver is the lobule, and each lobule consists of hepatic cellular plates which encircle a central vein. Small bile canaliculi bisect the plates and empty into ducts found in septa between the lobules. Hepatic sinusoids associated with the septa are lined with endothelial and Kupffer cells. Bacteria and organic matter are removed from the portal blood by the Kupffer cells which also express high levels of class II major histocompatibility complex proteins and release nitric oxide, interleukin (IL)-1, IL-6, and TNF.

Although they do not normally produce erythrocytes or divide in adults, liver cells are basically embryonic. If a portion of the liver is destroyed or removed, the remaining parenchyma can regenerate the entire organ. Liver cells are characterized by large amounts of endoplasmic reticulum which is consistent with their metabolic, storage, endo- and exo-cytotic activities. The liver has three main functions: 1) vascular, for the storage and filtration of blood; 2) metabolic, for regulation of glucose and storage of glycogen and fat; and 3) secretory/excretory, for regulation of hormones and degradation of toxic substances.

The normal blood volume of the liver is 450 ml, and an average blood flow through the liver is 1450 ml/min. The liver can store an extra 500–1000 ml of blood or supply extra blood after trauma. Half of the lymph produced in the body comes from the liver via drainage through the spaces of Disse (located below the hepatic cells). High blood pressure within the liver is a significant factor in edema or ascites.

Liver cells have a very high rate of metabolism; and they process, synthesize and degrade carbohydrates, fats and proteins simultaneously. Carbohydrate metabolism consists of storage of glycogen, conversion of fructose and galactose to glucose, and gluconeogenesis. The liver regulates the amount of glucose in the blood in response to hormones.

Liver cells have special fat-metabolizing functions, the oxidation of fatty acids and the production of lipoproteins, phospholipids and cholesterol. The lipoproteins transport phospholipids and cholesterol to other areas where they are used to form cellular membranes and other substances important in cellular function. Most of the conversion of carbohydrates and proteins to fat occurs in the liver although storage may be in adipose tissue elsewhere in the body. The liver also stores the fat-soluble vitamins and iron.

The liver forms 90% of the plasma proteins, particularly albumin and various globulins, at the rate of 15–50 g/day. The liver also produces haptoglobin, ceruloplasmin, and transferrin in response to cytokines. It manufactures nonessential amino acids; and in the presence of vitamin K, synthesizes accelerator globulin, erythropoietin, and the clotting factors I, II, V, VII, IX and X.

Lipid-soluble drugs are usually detoxified in the liver. Phase I reactions involve enzymatic modification of reactive groups on drug molecules by oxidation, reduction, hydroxylation, sulfoxidation, deamination, dealkylation or methylation. Such modifications deactivate barbiturates and benzodiazepines and activate cortisone or prednisone. The enzymes responsible for phase I reactions are induced by ethanol and barbiturates and inhibited by chloramphenicol, cimetidine and ethanol.

Phase II reactions involve enzymatic conversion of substances to their acid or salt derivatives, e.g., glucuronide, glycine, or sulfate. When the liver is damaged, it is slower in processing of anticonvulsants (phenobarbital), anti-inflammatory agents (acetaminophen or glucocorticoids), tranquilizers (lidocaine, propranolol) or antibiotics (chloramphenicol, tetracycline, or rifampin). In addition, the liver inactivates endogenous hormones by deamination, proteolysis, or deiodination. Glucocorticoids and aldosterone are reduced to their tetrahydro derivative and conjugated to glucuronic acid. Testosterone and estrogen are converted to ketosteroids and conjugated with sulfates or glucuronic acid.

Abnormal physiologic or pathologic conditions of the liver include fatty liver, which is the excessive accumulation of lipids in hepatocytes in response to injury; jaundice, in which large quantities of bilirubin are present in the extracellular fluid; hepatitis, which are viral infections caused by hepadnaviruses but whose major pathology results from host immunologic response; cirrhosis, which is caused by irreversible chronic injury of hepatic parenchyma and progresses to fibrosis; infiltrative diseases such as granulomas and amyloidosis; and adenomas and carcinomas.

Clinicians currently evaluate bilirubin and urobilinogen levels to diagnose hemolytic liver disease and assay carcinoembryonic antigen level to diagnose metastatic cancer. Depending on its function, an assay for thrombin receptor homolog could become a diagnostic tool for excessive fibrosis and resulting liver damage. If the thrombin receptor homolog is expressed in response to mechanical or chemical injury or involved in unnecessary clotting reactions or progressive fibrosis, then it may also represent an accessible therapeutic target for controlling inflammatory processes in the liver.

Liver anatomy, physiology, and diseases are reviewed, inter alia, in Guyton, A. C. (1991) Textbook of Medical Physiology, W. B. Saunders Co, Philadelphia, Pa.; Isselbacher, K. J. et al (1994) Harrison's Principles of Internal Medicine, McGraw-Hill, New York City; and The Merck Manual of Diagnosis and Therapy (1992) Merck Research Laboratories, Rahway, N.J.

SUMMARY OF THE INVENTION

The subject invention provides a unique nucleotide sequence, SEQ ID NO:1, which encodes a novel human thrombin receptor homolog (TRH), SEQ ID NO:2. The cDNA, herein designated trh, was identified and cloned using Incyte Clone No. 86700 from a liver cDNA library.

The invention also comprises the use of this TRH or its variants to intercede in physiologic or pathologic conditions and include diagnosis or therapy of activated or inflamed cells and/or tissues with trh nucleic acids, fragments or oligomers thereof. Aspects of the invention include the antisense DNA of trh; cloning or expression vectors containing trh; host cells or organisms transformed with expression vectors containing trh; a method for the production and recovery of purified TRH from host cells; purified protein, TRH, which can be used to identify antagonists, antibodies or inhibitors of the receptor for therapeutic use.

DESCRIPTION OF THE FIGURES

FIGS. 1A and 1B show the nucleotide and amino acid alignments of the extended sequences for TRH. The oligomers used to extend the nucleotide sequence to full length are XLR=AAGGAGGGCATAATTCCACAATGTG and XLF=AAGGAGGGCATAATTCCACAATGTG.

FIGS. 2A, 2B, and 2C display the alignment of human TRH with HUMTHRR, human thrombin receptor. Note the presence of the conserved arg[41] and ser[42] cleavage site.

DETAILED DESCRIPTION OF THE INVENTION

Definitions

As used herein, TRH, refers to thrombin receptor homologs, naturally occurring TRHs and active fragments thereof, which have essentially the amino acid sequence shown in SEQ ID NO: 2. In one embodiment, the polypeptide TRH is encoded by mRNAs transcribed from the cDNA (trh) of SEQ ID NO: 1.

"Active" refers to those forms of TRH which retain the biologic and/or immunologic activities of any naturally occurring TRH.

"Naturally occurring TRH" refers to TRHs produced by human cells that have not been genetically engineered and specifically contemplates various TRHs arising from post-translational modifications of the polypeptide including but not limited to acetylation, carboxylation, glycosylation, phosphorylation, lipidation and acylation.

"Derivative" refers to TRHs chemically modified by such techniques as ubiquitination, labeling (e.g., with radionuclides, various enzymes, etc.), pegylation (derivatization with polyethylene glycol), and insertion or substitution by chemical synthesis of amino acids such as ornithine, which do not normally occur in human proteins.

"Recombinant polypeptide variant" refers to any polypeptide having the activity of the TRH polypeptide and differing from naturally occurring TRHs by amino acid insertions, deletions, and substitutions created using recombinant DNA techniques. Guidance in determining which amino acid residues may be replaced, added or deleted without abolishing activities of interest, such as normal signal transduction, may be found by comparing the sequence of the particular TRH with that of homologous peptides and minimizing the number of amino acid sequence changes made in highly conserved regions.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative replacements. "Insertions" or "deletions" are typically in the range of about 1 to 5 amino acids. The variation allowed may be experimentally determined by producing the peptide synthetically or by systematically making insertions, deletions, or substitutions of nucleotides in a trh molecule using recombinant DNA techniques and assaying the expressed, recombinant variants for activity.

A polypeptide "fragment", "portion", or "segment" is a stretch of amino acid residues of at least 5 amino acids and as many as about 20 amino acids, preferably about 9 to 13 amino acids. To be active, any TRH fragment must have sufficient length to display biologic and/or immunologic activity either alone or as part of a chimeric display molecule such as keyhole limpet hemocyanin for antibody production or a chimeric test molecule consisting mostly of a purinergic receptor for evaluating activity.

Where desired, a "signal or leader sequence" can direct the polypeptide through the membrane of a cell. Such a sequence may be naturally present on the polypeptides of the present invention or provided from heterologous sources by recombinant DNA techniques.

"Probe" is an RNA or DNA of sufficient length of use in molecular amplification or hybridization to detect complementary sequences.

An "oligonucleotide" or "oligomer" is a stretch of nucleotide residues which has a sufficient number of bases to be used as a primer or probe in a polymerase chain reaction (PCR). Such oligonucleotides are prepared based on the t7g cDNA sequence which is found in the Sequence Listing. After appropriate testing to establish reaction conditions and to eliminate false positives, they are used to amplify, reveal or confirm the presence of an identical or homologous DNA or its transcribed RNA in a particular cell or tissue. Oligonucleotides or oligomers comprise portions of a DNA sequence having at least about 10 nucleotides and as many as about 35 nucleotides, preferably about 25 nucleotides. "Degenerate oligonucleotide probes" are probes in which minor substitutions based on the degeneracy of the genetic code (more than one codon may specify the same amino acid) have been made. They are particularly useful in the amplification of a similar natural nucleic acid sequence from chromosomal DNA as described by Walsh P. S. et al (1992, PCR Methods Appl 1:241–50).

A "portion" or "fragment" of a polynucleotide or nucleic acid comprises all or any part of the nucleotide sequence of a t7g having fewer nucleotides than about 6 kb, preferably fewer than about 1 kb which can be labelled and used as probe. A probe may be labelled with a radioactive element, an enzyme, or a chromogenic or fluorogenic marker. After appropriate testing to establish reaction conditions and to eliminate false positives, nucleic acid probes may be used in Southern, northern or in situ hybridizations to determine whether DNA or RNA encoding a particular T7G or T7G homolog are present in a particular cell type, tissue, or organ.

Although the sequences for nucleic acid probes may be derived from naturally occurring, recombinant or computer consensus sequences, the physical probe may be chemically synthesized, entirely or in part, and labeled by nick translation, Klenow fill-in reaction, PCR or other methods well known in the art. Probes of the present invention, their preparation and/or labeling are elaborated in Sambrook J. et al (1989) Molecular Cloning: A Laboratory Manual, Cold Spring Harbor Laboratory, Cold Spring Harbor, N.Y.; or Ausubel F. M. et al (1989) Current Protocols in Molecular Biology, John Wiley & Sons, New York City, both incorporated herein by reference.

"Recombinant nucleotide variants" encoding T7Gs may be synthesized or selected by making use of the "redundancy" in the genetic code. Various codon substitutions, such as the silent changes which produce specific restriction sites, may be introduced to optimize cloning into a plasmid or viral vector or to increase expression in a particular prokaryotic or eukaryotic system. Codon usage-specific mutations may also be introduced or chimeras containing the domains of related peptides added to test or modify the properties of any part of the polypeptide, particularly to change ligand-binding affinities, interchain affinities, or degradation/turnover rate.

DETAILED DESCRIPTION OF THE INVENTION

The present invention provides a unique nucleotide sequence identifying a novel homolog of human thrombin receptor which was first identified among the cDNAs of a liver library. The sequence for trh is shown in SEQ ID NO: 1 and is homologous to but significantly different from the GenBank sequence, HUMTHRR. Because TRH may be expressed in cells responding to trauma or infection, the nucleic acid (trh), polypeptide (TRH) and antibodies to TRH are useful in investigations of and interventions in the normal and abnormal physiologic and pathologic processes which regulate cell signalling, immunity, repair, etc. Therefore, an assay for upregulated expression of TRH can accelerate diagnosis and proper treatment of conditions caused by abnormal signal transduction due to systemic and local infections, traumatic and other tissue damage, hereditary or environmental diseases associated with hypertension, carcinomas, and other pathologic problems.

The nucleotide sequence encoding TRH (or its complement) has numerous other applications in techniques known to those skilled in the art of molecular biology. These techniques include use as hybridization probes for Southerns or northerns, use as oligomers for PCR, use for chromosomal and gene mapping, use in the recombinant production of TRH, use in generation of anti-sense DNA or RNA, their chemical analogs and the like, and use in production of chimeric molecules for selecting agonists, inhibitors or antagonists for design of domain-specific therapeutic molecules. Uses of the nucleotides encoding TRH disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of TRH-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring TRH, and all such variations are to be considered as being specifically disclosed.

Although nucleotide sequences which encode TRH and its variants are preferably capable of hybridizing to the nucleotide sequence of the naturally occurring TRH gene under stringent conditions, it may be advantageous to produce nucleotide sequences encoding TRH or its derivatives possessing a substantially different codon usage. Codons can be selected to increase the rate at which expression of the peptide occurs in a particular prokaryotic or eukaryotic host in accordance with the frequency with which particular codons are utilized by the host. Other reasons for substantially altering the nucleotide sequence encoding TRH and its derivatives without altering the encoded amino acid sequence include the production of RNA transcripts having more desirable properties, such as a greater half-life, than transcripts produced from the naturally occurring sequence.

The nucleotide sequence encoding TRH may be joined to a variety of other nucleotide sequences by means of well established recombinant DNA techniques (cf Sambrook J. et al, supra). Useful nucleotide sequences for joining to trh include an assortment of cloning vectors—plasmids, cosmids, lambda phage derivatives, phagemids, and the like—that are well known in the art and may be chosen for such characteristics as the size insert they can accommodate, their utility, their fidelity, etc. Other vectors of interest include expression vectors, replication vectors, probe generation vectors, sequencing vectors, YAC and BAC mapping vectors, and the like. In general, these vectors may contain an origin of replication functional in at least one organism, convenient restriction endonuclease sensitive sites, and selectable markers for the host cell.

Another aspect of the subject invention is to provide for trh-specific nucleic acid hybridization probes capable of hybridizing with naturally occurring nucleotide sequences encoding TRH. Such probes may also be used for the detection of TRH-encoding sequences and should preferably contain at least 50% of the nucleotides from any particular domain of interest from this trh encoding sequence. The hybridization probes of the subject invention may be derived from the nucleotide sequence of the SEQ ID NO: 1 or from genomic sequence including promoter, enhancer elements and introns of the respective naturally occurring trh. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR, as described in U.S. Pat. Nos 4,683,195; 4,800,195; and 4,965,188, provides additional uses for oligonucleotides based upon the nucleotide sequences which encode TRH. Such probes used in PCR may be of recombinant origin, may be chemically synthesized, or may be a mixture of both and comprise a discrete nucleotide sequence for diagnostic use or a degenerate pool of possible sequences for identification of closely related T7G sequences.

Full length genes may be cloned from known sequence using a new method which employs XL-PCR (Perkin-Elmer, Foster City, Calif.) to amplify long pieces of DNA. This method was developed to allow a single researcher to process multiple genes (up to 20 or more) at a time and to obtain an extended (possibly full-length) sequence within 6-10 days. It replaces current methods which use labelled probes to screen libraries and allow one researcher to process only about 3-5 genes in 14-40 days.

In the first step, which can be performed in about two days, primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones. If the full length cDNA has not been obtained, the entire procedure is repeated using either the original library or some other preferred library. The preferred library may be one that has been size-selected to include only larger cDNAs or may consist of single or combined commercially available libraries, e.g. lung, liver, heart and brain from Gibco/BRL (Gaithersburg Md.). The cDNA library may have been prepared with oligo dT or random primers. The advantage of using random primed libraries is that they will have more sequences which contain 5' ends of genes. A randomly primed library may be particularly useful if an oligo dT library does not yield a complete gene. Obviously, the larger the protein, the less likely it is that the complete gene will be found in a single plasmid.

Other means for producing hybridization probes for T7G DNAs include the cloning of nucleic acid sequences encoding TRH or its derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate labeled nucleotides.

It is now possible to produce a DNA sequence, or portions thereof, encoding TRH and/or its derivatives entirely by synthetic chemistry. Such molecules can be inserted into any of the many available vectors using reagents and methods that are known in the art at the time of the filing of this application. Moreover, synthetic chemistry may be used to introduce mutations into the trh sequences or any portion thereof.

The nucleotide sequence can be used to develop an assay to detect activation, inflammation, or disease associated with abnormal levels of TRH expression. The nucleotide sequence can be labeled by methods known in the art and added to a fluid or tissue sample from a patient. After an incubation period sufficient to effect hybridization, the sample is washed with a compatible fluid which contains a visible marker, a dye or other appropriate molecule(s), if the nucleotide has been labeled with an enzyme. After the compatible fluid is rinsed off, the dye is quantitated and compared with a standard. If the amount of dye is significantly elevated (or lowered, as the case may be), the nucleotide sequence has hybridized with the sample, and the assay indicates an abnormal condition such as inflammation or disease.

The nucleotide sequence for trh can be used to construct hybridization probes for mapping the gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of trh on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

The nucleotide sequence encoding TRH may be used to produce purified TRH using well known methods of recombinant DNA technology. Among the many publications that teach methods for the expression of genes after they have been isolated is Goeddel (1990) Gene Expression Technology, Methods and Enzymology, Vol 185, Academic Press, San Diego, Calif. TRH may be expressed in a variety of host cells, either prokaryotic or eukaryotic. Host cells may be from the same species in which trh nucleotide sequences are endogenous or from a different species. Advantages of producing TRH by recombinant DNA technology include obtaining adequate amounts of the protein for purification and the availability of simplified purification procedures.

Cells transformed with DNA encoding TRH may be cultured under conditions suitable for the expression of TRH and recovery of the protein from the cell culture. TRH produced by a recombinant cell may be secreted or may be contained intracellularly depending on the particular genetic construction used. In general, it is more convenient to prepare recombinant proteins in secreted form. Purification steps vary with the production process and the particular protein produced.

Various methods for the isolation of TRH polypeptide may be accomplished by procedures well known in the art. For example, such a polypeptide may be purified by immunoaffinity chromatography by employing the antibodies provided by the present invention. Various other methods of protein purification well known in the art include those described in Deutscher M (1990) Methods in Enzymology, Vol 182, Academic Press, San Diego, Calif.; and in Scopes R (1982) Protein Purification: Principles and Practice, Springer-Verlag, New York City, both incorporated herein by reference.

In addition to recombinant production, fragments of TRH may be produced by direct peptide synthesis using solid-phase techniques (cf Stewart et al (1969) Solid-Phase Peptide Synthesis, W. H. Freeman Co, San Francisco, Calif.; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (ABI, Foster City, Calif.) in accordance with the instructions provided by the manufacturer. Various fragments of TRH may be chemically synthesized separately and combined using chemical methods to produce the full length polypeptide.

TRH for antibody induction does not require biological activity; however, the protein must be immunogenic. Peptides used to induce specific antibodies may have an amino acid sequence consisting of at least five amino acids, preferably at least 10 amino acids. They should mimic an exposed structural portion or epitope of the amino acid sequence of the polypeptide and may contain the entire amino acid sequence of a small domain of TRH. Short stretches of TRH amino acids may be fused with those of another protein such as keyhole limpet hemocyanin, and antibody produced against the fusion protein.

Antibodies specific for TRH may be produced by inoculation of an appropriate animal with the polypeptide or an antigenic fragment. An antibody is specific for TRH if it is specific for an immunogenic epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R. et al (1989) PNAS 86:3833–37, or Huse W. D. et al (1989) Science 256:1275–81) or the in vitro stimulation of lymphocyte populations. Current technology (Winter G and Milstein C (1991) Nature 349:293–99) provides for a number of highly specific binding reagents based on the principles of antibody formation. These techniques may be adapted to produce molecules specifically binding particular domains of TRH.

An additional embodiment of the subject invention is the use of TRH specific antibodies or the like as bioactive agents to treat abnormal signal transduction due to systemic and local infections, traumatic and other tissue damage, hereditary or environmental diseases associated with hypertension, carcinomas, and other pathologic problems.

Bioactive compositions comprising agonists, antagonists, or inhibitors of TRH may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered by intravenous infusion into the bloodstream or any other effective means which could be used for treatment.

The examples below are provided to describe the subject invention. These examples are provided by way of illustration and are not included for the purpose of limiting the invention.

EXAMPLES

I Isolation of mRNA and Construction of the cDNA Library

The TRH sequence of this application was first identified in Incyte clone No. 86700 among the sequences comprising the human liver library. The human cells used for this library came from a 49 year old human male (Catalogue #937224; Stratagene, LaJolla, Calif.). cDNA synthesis for the cDNA library was primed with oligo dT, and synthetic adaptor oligonucleotides were ligated onto cDNA ends enabling its insertion into Uni-ZAP™ vector system (Stratagene). This allowed high efficiency unidirectional (sense orientation) lambda library construction and the convenience of a plasmid system with blue/white color selection to detect clones with cDNA insertions.

The cDNA library can be screened with either DNA probes or antibody probes and the pBluescript® phagemid (Stratagene) can be rapidly excised in vivo. The phagemid allows the use of a plasmid system for easy insert characterization, sequencing, site-directed mutagenesis, the creation of unidirectional deletions and expression of fusion polypeptides. The custom-constructed library phage particles were infected into E. coli host strain XL1-Blue® (Stratagene), which has a high transformation efficiency, increasing the probability of obtaining rare, under-represented clones in the cDNA library. Alternative unidirectional vectors include but are not limited to pcDNAI (Invitrogen, San Diego, Calif.) and pSHlox-1 (Novagen, Madison Wis.).

II Isolation of cDNA Clones

The phagemid forms of individual cDNA clones were obtained by the in vivo excision process, in which the host bacterial strain was coinfected with both the library phage and an f1 helper phage. Polypeptides or enzymes derived from both the library-containing phage and the helper phage nicked the DNA, initiated new DNA synthesis from defined sequences on the target DNA and created a smaller, single stranded circular phagemid DNA molecule that included all DNA sequences of the pBLUESCRIPT® plasmid and the cDNA insert. The phagemid DNA was secreted from the cells and purified, then used to re-infect fresh host cells, where double stranded phagemid DNA was produced. Because the phagemid carries the gene for β-lactamase, the newly transformed bacteria were selected on medium containing ampicillin.

Phagemid DNA was purified using the MAGIC MINI-PREPS™ DNA Purification System (Catalogue #A7100;

Promega Corp, Madison, Wis.). This small-scale process provides a simple and reliable method for lysing the bacterial cells and rapidly isolating purified phagemid DNA using a proprietary DNA-binding resin. Phagemid DNA was also purified using the QIAWELL-8 Plasmid Purification System (QIAGEN Inc, Chatsworth, Calif.). This product line provides a convenient, rapid high-throughput method for lysing the bacterial cells and isolating highly purified phagemid DNA using QIAGEN anion-exchange resin particles. Following either purification method, the DNA was eluted and prepared for sequencing and other analytical manipulations.

III Sequencing of cDNA Clones

The cDNA inserts from random isolates of the liver library were sequenced in part. Methods for DNA sequencing are well known in the art. Conventional enzymatic methods employed DNA polymerase Klenow fragment, SEQUENASE® (U.S. Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Catalyst 800 and the Applied Biosystems 377 or 373 DNA sequencers.

IV Homology Searching of cDNA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S. F. (1993) J Mol Evol 36:290–300; Altschul, S. F. et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Identification, Full Length Cloning, Sequencing and Translation

Analysis of INHERIT™ results from randomly picked and sequenced portions of clones from liver library identified Incyte 86700 as a homolog of the thrombin receptor, HUMTHRR. The cDNA insert comprising Incyte 86700 was fully sequenced and used as the basis for cloning the full length cDNA.

The cDNA of Incyte 86700 was extended to full length using a modified XL-PCR (Perkin Elmer) procedure. Primers were designed based on known sequence; one primer was synthesized to initiate extension in the antisense direction (XLR=TGCCTTCCGTTG CTGTATAGACCG) and the other to extend sequence in the sense direction (XLF= AAGGAGGGCATAATTCCACAATGTG). The primers allowed the sequence to be extended "outward" generating ampiicons containing new, unknown nucleotide sequence for the gene of interest. The primers were designed using Oligo 4.0 (National Biosciences Inc, Plymouth, Minn.) to be 22–30 nucleotides in length, to have a GC content of 50% or more, and to anneal to the target sequence at temperatures about 68°–72° C. Any stretch of nucleotides which would result in hairpin structures and primer-primer dimerizations were avoided.

The liver cDNA library was used as a template, and XLR and XLF primers were used to extend and amplify the 86700 sequence. By following the instructions for the XL-PCR kit and thoroughly mixing the enzyme and reaction mix, high fidelity amplification is obtained. Beginning with 25 pMol of each primer and the recommended concentrations of all other components of the kit, PCR was performed using the MJ thermocycler PTC200 (MJ Research, Watertown Mass.) and the following parameters:

| Step    | |
|---------|---|
| Step 1  | 94° C. for 60 sec (initial denaturation) |
| Step 2  | 94° C. for 15 sec |
| Step 3  | 65° C. for 1 min |
| Step 4  | 68° C. for 7 min |
| Step 5  | Repeat step 2–4 for 15 additional times |
| Step 6  | 94° C. for 15 sec |
| Step 7  | 65° C. for 1 min |
| Step 8  | 68° C. for 7 min + 15 sec/cycle |
| Step 9  | Repeat step 6–8 for 11 additional times |
| Step 10 | 72° C. for 8 min |
| Step 11 | 4° C. (and holding) |

At the end of 28 cycles, 50 μl of the reaction mix was removed; and the remaining reaction mix was run for an additional 10 cycles as outlined below:

| Step 1 | 94° C. for 15 sec |
| Step 2 | 65° C. for 1 min |
| Step 3 | 68° C. for (10 min + 15 sec)/cycle |
| Step 4 | Repeat step 1–3 for 9 additional times |
| Step 5 | 72° C. for 10 min |

A 5–10 µl aliquot of the reaction mixture was analyzed by electrophoresis on a low concentration (about 0.6–0.8%) agarose mini-gel to determine which reactions were successful in extending the sequence. Although all extensions potentally contain a full length gene, some of the largest products or bands were selected and cut out of the gel. Further purification involved using a commercial gel extraction method such as QIAQuick™ (QIAGEN Inc, Chatsworth, Calif.). After recovery of the DNA, Klenow enzyme was used to trim single-stranded, nucleotide overhangs creating blunt ends which facilitated religation and cloning.

After ethanol precipitation, the products were redissolved in 13 µl of ligation buffer. Then, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook J. et al, supra). After incubation for one hour at 37° C., the whole transformation mixture was plated on Luria Bertani (LB)-agar (Sambrook J. et al, supra) containing carbenicillin at 25 mg/L. The following day, 12 colonies were randomly picked from each plate and cultured in 150 µl of liquid LB/carbenicillin medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 15 µl of concentrated PCR reaction mix (1.33x) containing 0.75 units of Taq polymerase, a vector primer and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 times |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid and sequenced.

Figure 2A:
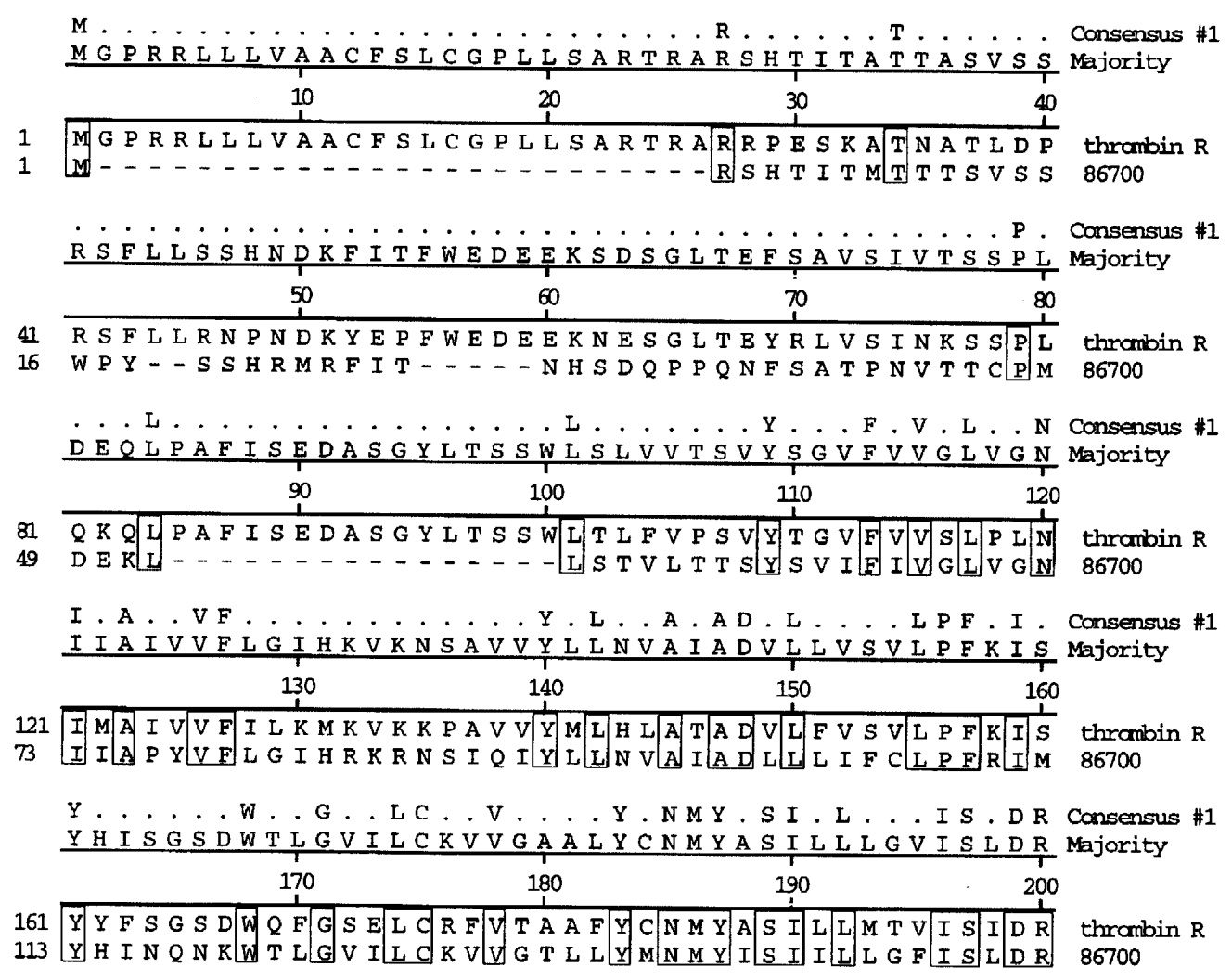

The cDNA (SEQ ID NO 1) and amino acid (SEQ ID NO 2) sequences for human TRH are shown in FIG. 1. When the three possible translations of TRH were searched against protein databases such as SwissProt and PIR, no exact matches were found. FIG. 2 shows the comparison between the trh and HUMTHRR sequences.

VI Antisense analysis

Knowledge of the correct, complete cDNA sequence of TRH enables its use as a tool for antisense technology in the investigation of gene function. Oligonucleotides, cDNA or genomic fragments comprising the antisense strand of trh can be used either in vitro or in vivo to inhibit expression of the mRNA. Such technology is now well known in the art, and antisense molecules can be designed at various locations along the nucleotide sequences. By treatment of cells or whole test animals with such antisense sequences, the gene of interest can be effectively turned off. Frequently, the function of the gene can be ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of TRH

Expression of trh may be accomplished by subcloning the cDNAs into appropriate expression vectors and transfecting the vectors into analogous expression hosts. In this particular case, the cloning vector previously used for the generation of the cDNA library also provides for direct expression of trh sequences in *E. coli*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or the inclusion of an oligonucleotide linker of appropriate length.

The trh cDNA can be shuttled into other vectors known to be useful for expression of protein in specific hosts. Oligonucleotide primers containing cloning sites as well as a segment of DNA (about 25 bases) sufficient to hybridize to stretches at both ends of the target cDNA can be synthesized chemically by standard methods. These primers can then be used to amplify the desired gene segment by PCR. The resulting gene segment can be digested with appropriate restriction enzymes under standard conditions and isolated by gel electrophoresis. Alternately, similar gene segments can be produced by digestion of the cDNA with appropriate restriction enzymes. Using appropriate primers, segments of coding sequence from more than one gene can be ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells, insect cells such as Sf9 cells, yeast cells such as *Saccharomyces cerevisiae*, and bacteria such as *E. coil*. For each of these cell systems, a useful expression vector may also include an origin of replication to allow propagation in bacteria and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, may be used in mammalian host cells. Once homogeneous cultures of recombinant cells are obtained through standard culture methods, large quantities of recombinantly produced TRH can be recovered from the conditioned medium and analyzed using chromatographic methods known in the art.

VIII Isolation of Recombinant TRH

TRH may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase (Invitrogen, San Diego, Calif.) between the purification domain and the trh sequence may be useful to facilitate expression of TRH.

IX Testing of Chimerio T7Gs

Functional chimeric T7Gs may be constructed by combining the extracellular receptive sequences of a new isoform with the transmembrane and intracellular segments of a known isoform for testing purposes. This concept was demonstrated by Kobilka et al (1988, Science 240:1310–1316) who created a series of chimeric α2-β2 adrenergic receptors (AR) by inserting progressively greater amounts of α2-AR transmembrane sequence into β2-AR. The binding activity of known agonists changed as the molecule shifted from having more α2 than β2 conformation, and intermediate constructs demonstrated mixed specificity. The specificity for binding antagonists, however, correlated with the source of the domain VII. The importance of T7G domain VII for ligand recognition was also found in chimeras utilizing two yeast α-factor receptors and is significant because the yeast receptors are classified as miscellaneous receptors. Thus, functional role of specific domains appears to be preserved throughout the T7G family regardless of category.

In parallel fashion, internal segments or cytoplasmic domains from a particular isoform may be exchanged with the analogous domains of a known T7G and used to identity the structural determinants responsible for coupling the receptors to trimeric G-proteins (Dohlman et al (1991) Annu Rev Biochem 60:653–88). A chimeric receptor in which domains V, VI, and the intracellular connecting loop from β2-AR were substituted into α2-AR was shown to bind ligands with α2-AR specificity, but to stimulate adenylate cyclase in the manner of β2-AR. This demonstrates that for adrenergic-type receptors, G-protein recognition is present in domains V and VI and their connecting loop. The opposite situation was predicted and observed for a chimera in which the V→VI loop from α1-AR replaced the corresponding domain on β2-AR and the resulting receptor bound ligands with β2-AR specificity and activated G-protein-mediated phosphatidylinositol turnover in the α1-AR manner. Finally, chimeras constructed from muscarinic receptors also demonstrated that V→VI loop is the major determinant for specificity of G-protein activity (Bolander F. F., supra).

Chimeric or modified T7Gs containing substitutions in the extracellular and transmembrane regions have shown that these portions of the receptor determine ligand binding specificity. For example, two Ser residues conserved in domain V of adrenergic and D catecholamine T7G receptors are necessary for potent agonist within the T7G binding believed to form hydrogen bonds with the catechol moiety of the agonists within the T7G binding site. Similarly, an Asp residue present in domain III of all T7Gs which bind biogenic amines is believed to form an ion pair with the ligand amine group in the T7G binding site.

Functional, cloned T7Gs may be expressed in heterologous expression systems and their biological activity assessed (cf Marullo et al (1988) Proc Natl Acad Sci 85:7551–55; King et al (1990) Science 250:121–23). One heterologous system introduces genes for a mammalian T7G and a mammalian G-protein into yeast cells. The T7G was shown to have appropriate ligand specificity and affinity and trigger appropriate biological activation- growth arrest and morphological changes—of the yeast cells. THR domains may be tested in a similar manner.

X Production of TRH Specific Antibodies

Two approaches are utilized to raise antibodies to TRH, and each approach is useful for generating either polyclonal or monoclonal antibodies. In one approach, denatured protein from reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of an appropriate TRH domain, as deduced from translation of the cDNA, is analyzed to determine regions of high immunogenicity. Oligopeptides comprising appropriate hydrophilic regions, as illustrated in FIG. 3, are synthesized and used in suitable immunization protocols to raise antibodies. Analysis to select appropriate epitopes is described by Ausubel F. M. et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St Louis, Mo.) by reaction with M-maleimidobenzoyl-N-hydroxysuccinimide ester (MBS; cf. Ausubel F. M. et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled TRH to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable anti-species Ig) antibodies at 10 mg/ml. The coated wells are blocked with 1% BSA, washed and incubated with supernatants from hybridomas. After washing the wells are incubated with labeled TRH at 1 rag/ml. Supernatants with specific antibodies bind more labeled TRH than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ or stronger, will typically be made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

XI Diagnostic Test Using TRH Specific Antibodies

Particular TRH antibodies are useful for investigating signal transduction and the diagnosis of infectious or hereditary conditions which are characterized by differences in the amount or distribution of TRH or downstream products of an active signalling cascade. Since TRH was found in a human liver library, it appears to be upregulated in cell types mainly involved in immune protection or defense.

Diagnostic tests for TRH include methods utilizing antibody and a label to detect TRH in human body fluids, membranes, cells, tissues or extracts of such. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound TRH, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on TRH is preferred, but a competitive binding assay may be employed. These assays are described, among other places, in Maddox, D. E. et al (1983, J Exp Med 158:1211f).

XII Purification of Native TRH Using Specific Antibodies

Native or recombinant TRH can be purified by immunoaffinity chromatography using antibodies specific for TRH. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns may be utilized in the purification of TRH by preparing a fraction from cells containing TRH in a soluble form. This preparation may be derived by solubilization of whole cells or of a subcellular fraction obtained via differental centrifugation (with or without addition of detergent) or by other methods well known in the art. Alternatively, soluble TRH containing a signal sequence may be secreted in useful quantity into the medium in which the cells are grown.

A soluble TRH-containing preparation is passed over the immunoaffinity column, and the column is washed under conditions that allow the preferential absorbance of TRH (e.g., high ionic strength buffers in the presence of detergent). Then, the column is eluted under conditions that disrupt antibody/TRH binding (e.g., a buffer of pH 2–3 or a high concentration of a chaotrope such as urea or thiocyanate ion), and TRH is collected.

XIII Drug Screening

This invention is particularly useful for screening therapeutic compounds by using TRH or binding fragments thereof in any of a variety of drug screening techniques. The polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between TRH and the agent being tested. Alternatively, one can examine the diminution in complex formation between TRH and a receptor caused by the agent being tested.

Thus, the present invention provides methods of screening for drugs or any other agents which can affect signal transduction. These methods, well known in the art, comprise contacting such an agent with TRH polypeptide or a fragment thereof and assaying (i) for the presence of a complex between the agent and the TRH polypeptide or fragment, or (ii) for the presence of a complex between the TRH polypeptide or fragment and the cell. In such competitive binding assays, the TRH polypeptide or fragment is typically labeled. After suitable incubation, free TRH polypeptide or fragment is separated from that present in bound form, and the amount of free or uncomplexed label is a measure of the ability of the particular agent to bind to TRH or to interfere with the TRH and agent complex.

Another technique for drug screening provides high throughput screening for compounds having suitable binding affinity to the TRH polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with TRH polypeptide and washed. Bound TRH polypeptide is then detected by methods well known in the art. Purified TRH can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding TRH specifically compete with a test compound for binding to TRH polypeptides or fragments thereof. In this manner, the antibodies can be used to detect the presence of any peptide which shares one or more antigenic determinants with TRH.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf. Hodgson J. (1991) Bio/Technology 9:19-21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design efficient inhibitors. Useful examples of rational drug design may include molecules which have improved activity or stability as shown by Braxton S. and Wells J. A. (1992, Biochemistry 31:7796-7801) or which act as inhibitors, agonists, or antagonists of native peptides as shown by Athauda S. B. et al (1993 J Biochem 113:742-46), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id can then be used to identify and isolate peptides from banks of chemically or biologically produced peptides. The isolated peptides then act as the pharmacore.

By virtue of the present invention, sufficient amount of polypeptide may be made available to perform such analytical studies as X-ray crystallography. In addition, knowledge of the TRH amino acid sequence provided herein will provide guidance to those employing computer modeling techniques in place of or in addition to x-ray crystallography.

XV Identification of Other Members of the Signal Transduction Complex

The inventive purified TRH is a research tool for identification, characterization and purification of interacting G or other signal transduction pathway proteins. Radioactive labels are incorporated into a selected TRH domain by various methods known in the art and used in vitro to capture interacting molecules. A preferred method involves labeling the primary amino groups in TRH with $^{125}I$ Bolton-Hunter reagent (Bolton, A. E. and Hunter, W. M. (1973) Biochem J 133: 529). This reagent has been used to label various molecules without concomitant loss of biological activity (Hebert C. A. et al (1991) J Biol Chem 266: 18989; McColl S. et al (1993) J Immunol 150:4550-4555).

Labeled TRH is useful as a reagent for the purification of molecules with which it interacts. In one embodiment of affinity purification, membrane-bound TRH is covalently coupled to a chromatography column. Cell-free extract derived from liver cells or putative target cells is passed over the column, and molecules with appropriate affinity bind to TRH. The TRH-complex is recovered from the column, dissociated and the recovered molecule is subjected to N-terminal protein sequencing. This amino acid sequence is then used to identify the captured molecule or to design degenerate oligonucleotide probes for cloning the relevant gene from an appropriate cDNA library.

In an alternate method, antibodies are raised against TRH, specifically monoclonal antibodies. The monoclonal antibodies are screened to identify those which inhibit the binding of labeled TRH. These monoclonal antibodies are then used therapeutically.

XVI Use and Administration of Antibodies, Inhibitors, or Antagonists

Antibodies, inhibitors, or antagonists of TRH (or other treatments to limit signal transduction, LST), can provide different effects when administered therapeutically. LSTs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of LSTs include solubility of the molecule, half-life and antigenicity/immunogenicity; these and other characteristics may aid in defining an effective carrier. Native human proteins are preferred as LSTs, but organic or synthetic molecules resulting from drug screens may be equally effective in particular situations.

LSTs may be delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the LST to be administered, and the pharmacokinetic profile of the particular LST. Additional factors which may be taken into account include disease state (e.g. severity) of the patient, age, weight, gender, diet, time and frequency of administration, drug combination, reaction sensitivities, and tolerance/response to therapy. Long acting LST formulations might be administered every 3 to 4 days, every week, or once every two weeks depending on half-life and clearance rate of the particular LST.

Normal dosage amounts may vary from 0.1 to 100,000 micrograms, up to a total dose of about 1 g, depending upon the route of administration. Guidance as to particular dosages and methods of delivery is provided in the literature.

See U.S. Pat. No. 4,657,760; 5,206,344; or 5,225,212. Those skilled in the art will employ different formulations for different LSTs. Administration to cells such as nerve cells necessitates delivery in a manner different from that to other cells such as vascular endothelial cells.

It is contemplated that abnormal signal transduction, trauma, or diseases which trigger TRH activity may be treatable with LSTs. These conditions or diseases may be specifically diagnosed by the tests discussed above, and such testing should be performed in suspected cases of systemic and local infections, traumatic and other tissue damage, hereditary or environmental diseases associated with hypertension, carcinoma, and other physiologic/pathologic problems.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

We claim:

1. An isolated and purified polynucleotide encoding a thrombin receptor homolog (TRH) comprising the amino acid sequence of SEQ ID NO:2.

2. The polynucleotide of claim 1 further comprising a control sequence for the the expression of TRH.

3. The polynucleotide of claim 1 comprising a recombinant DNA molecule whose nucleotide sequence is shown as SEQ ID NO 1.

4. An expression vector comprising the polynucleotide of claim 1.

5. A host cell transformed with the expression vector of claim 4.

6. A method for producing TRH, said method comprising the steps of:

a) culturing the host cell of claim 5 under conditions suitable for the expression of TRH; and b) recovering TRH from the cell culture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1143 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: Liver
( B ) CLONE: 86700

( x i ) SEQUENCE DESCRIPTION: SEQ ID NO:1:

```
ATGAGAAGTC ATACCATAAC AATGACGACA ACTTCAGTCA GCAGCTGGCC TTACTCCTCC        60
CACAGAATGC GCTTTATAAC CAATCATAGC GACCAACCGC CACAAAACTT CTCAGCAACA       120
CCAAATGTTA CTACCTGTCC CATGGATGAA AAATTGCTAT CTACTGTGTT AACCACATCC       180
TACTCTGTTA TTTTCATCGT GGGACTGGTT GGGAACATAA TCGCCCCCTA TGTATTTCTG       240
GGTATTCACC GTAAAAGAAA TTCCATTCAA ATTTATCTAC TTAACGTAGC CATTGCAGAC       300
CTCCTACTCA TCTTCTGCCT CCCTTTCCGA ATAATGTATC ATATTAACCA AAACAAGTGG       360
ACACTAGGTG TGATTCTGTG CAAGGTTGTG GGAACACTGC TTTATATGAA CATGTACATT       420
AGCATTATTT TGCTTGGATT CATCAGTTTG GATCGCTATA TAAAAATTAA TCGGTCTATA       480
CAGCAACGGA AGGCAATAAC AACCAAACAA AGTATTTATG TCTGTTGTAT AGTATGGATG       540
CTTGCTCTTG GTGGATTCCT AACTATGATT ATTTTAACAC TTAAGAAAGG AGGGCATAAT       600
TCCACAATGT GTTTCCATTA CAGAGATAAG CATAACGCAA AAGGAGAAGC CATTTTTAAC       660
TTCATTCTTG TGGTAATGTT CTGGCTAATT TTCTTACTAA TAATCCTTTC ATATATTAAG       720
ATTGGGAAGA ATCTATTGAG GATTTCTAAA AGGAGGTCAA AATTTCCTAA TTCTGGTAAA       780
TATGCCACTA CAGCTCGTAA CTCCTTTATT GTACTTATCA TTTTTACTAT ATGTGTGGGT       840
CCCTATCATG CCTTTCGATT CATCTACATT TCTTCACAGC TAAATGTATC ATCTTGCTAC       900
TGGAAAGAAA TTGTTCACAA AACCAATGAG ATCATGCTGG TTCTCTCATC TTTCAATAGT       960
TGGTTAGATC CAGTCATGTA TTTCCTGATG TCCAGTAACA TTCGCAAAAT AATGTGCCAA      1020
CTTCTTTTTA GACGATTTCA AGGTGAACCA AGTAGGAGTG AAAGCACTTC AGAATTTAAA      1080
CCAGGATACT CCCTGCATGA TACATCTGTG GCAGGGAAAA TACAGTCTAG TTCTGAAAGT      1140
```

(2) INFORMATION FOR SEQ ID NO:2:

(i) SEQUENCE CHARACTERISTICS:
        (A) LENGTH: 381 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Ser His Thr Ile Thr Met Thr Thr Thr Ser Val Ser Ser Trp
 1               5                  10                  15

Pro Tyr Ser Ser His Arg Met Arg Phe Ile Thr Asn His Ser Asp Gln
             20                  25                  30

Pro Pro Gln Asn Phe Ser Ala Thr Pro Asn Val Thr Thr Cys Pro Met
         35                  40                  45

Asp Glu Lys Leu Leu Ser Thr Val Leu Thr Thr Ser Tyr Ser Val Ile
     50                  55                  60

Phe Ile Val Gly Leu Val Gly Asn Ile Ile Ala Pro Tyr Val Phe Leu
65                  70                  75                  80

Gly Ile His Arg Lys Arg Asn Ser Ile Gln Ile Tyr Leu Leu Asn Val
                 85                  90                  95

Ala Ile Ala Asp Leu Leu Leu Ile Phe Cys Leu Pro Phe Arg Ile Met
             100                 105                 110

Tyr His Ile Asn Gln Asn Lys Trp Thr Leu Gly Val Ile Leu Cys Lys
         115                 120                 125

Val Val Gly Thr Leu Leu Tyr Met Asn Met Tyr Ile Ser Ile Ile Leu
     130                 135                 140

Leu Gly Phe Ile Ser Leu Asp Arg Tyr Ile Lys Ile Asn Arg Ser Ile
145                 150                 155                 160

Gln Gln Arg Lys Ala Ile Thr Thr Lys Gln Ser Ile Tyr Val Cys Cys
                 165                 170                 175

Ile Val Trp Met Leu Ala Leu Gly Gly Phe Leu Thr Met Ile Ile Leu
             180                 185                 190

Thr Leu Lys Lys Gly Gly His Asn Ser Thr Met Cys Phe His Tyr Arg
         195                 200                 205

Asp Lys His Asn Ala Lys Gly Glu Ala Ile Phe Asn Phe Ile Leu Val
     210                 215                 220

Val Met Phe Trp Leu Ile Phe Leu Leu Ile Ile Leu Ser Tyr Ile Lys
225                 230                 235                 240

Ile Gly Lys Asn Leu Leu Arg Ile Ser Lys Arg Arg Ser Lys Phe Pro
                 245                 250                 255

Asn Ser Gly Lys Tyr Ala Thr Thr Ala Arg Asn Ser Phe Ile Val Leu
             260                 265                 270

Ile Ile Phe Thr Ile Cys Val Gly Pro Tyr His Ala Phe Arg Phe Ile
         275                 280                 285

Tyr Ile Ser Ser Gln Leu Asn Val Ser Ser Cys Tyr Trp Lys Glu Ile
     290                 295                 300

Val His Lys Thr Asn Glu Ile Met Leu Val Leu Ser Ser Phe Asn Ser
305                 310                 315                 320

Trp Leu Asp Pro Val Met Tyr Phe Leu Met Ser Ser Asn Ile Arg Lys
                 325                 330                 335

Ile Met Cys Gln Leu Leu Phe Arg Arg Phe Gln Gly Glu Pro Ser Arg
             340                 345                 350
```

-continued

| Ser | Glu | Ser | Thr | Ser | Glu | Phe | Lys | Pro | Gly | Tyr | Ser | Leu | His | Asp | Thr |
|---|---|---|---|---|---|---|---|---|---|---|---|---|---|---|---|
| | | 355 | | | | | 360 | | | | | 365 | | | |
| Ser | Val | Ala | Gly | Lys | Ile | Gln | Ser | Ser | Ser | Glu | Ser | Thr | | | |
| | 370 | | | | | 375 | | | | | 380 | | | | |